United States Patent
Hafner et al.

(10) Patent No.: US 8,493,009 B2
(45) Date of Patent: Jul. 23, 2013

(54) SURGICAL MOTOR CONTROL DEVICE, SURGICAL DRIVE SYSTEM AND METHOD FOR CONTROLLING A SURGICAL DRIVE UNIT

(75) Inventors: Ronald Hafner, Leibertingen (DE); Ernst Moosmann, Leibertingen-Altheim (DE); Juergen Schneider, Tuttlingen (DE); Harald Konrath, Rottenburg a.N. (DE)

(73) Assignee: Aesculap AG, Tuttlingen (DE)

( * ) Notice: Subject to any disclaimer, the term of this patent is extended or adjusted under 35 U.S.C. 154(b) by 565 days.

(21) Appl. No.: 12/798,449

(22) Filed: Apr. 1, 2010

(65) Prior Publication Data

US 2010/0264864 A1    Oct. 21, 2010

(30) Foreign Application Priority Data

Apr. 8, 2009    (DE) .......................... 10 2009 018 143

(51) Int. Cl.
*H02P 1/04*    (2006.01)

(52) U.S. Cl.
USPC ............ 318/400.17; 318/400.32; 318/400.34; 318/400.35

(58) Field of Classification Search
USPC ............. 318/400.17, 400.32, 400.34, 400.35, 318/811
See application file for complete search history.

(56) References Cited

U.S. PATENT DOCUMENTS

| | | |
|---|---|---|
| 2,244,683 A | 6/1941 | Fisher |
| 3,750,068 A | 7/1973 | Hallin |
| 4,091,880 A | 5/1978 | Troutner et al. |
| 4,204,580 A | 5/1980 | Nalley |
| 4,848,146 A | 7/1989 | Bruno et al. |
| 5,107,151 A | 4/1992 | Cambier |
| 5,268,622 A | 12/1993 | Philipp |
| 5,467,911 A | 11/1995 | Tsuruta et al. |
| 5,625,545 A * | 4/1997 | Hammond ...................... 363/71 |
| 5,677,605 A | 10/1997 | Cambier et al. |
| 5,689,159 A * | 11/1997 | Culp et al. ............... 318/400.18 |
| 5,747,953 A | 5/1998 | Philipp |
| 5,852,554 A * | 12/1998 | Yamamoto ...................... 363/71 |
| 5,933,339 A | 8/1999 | Duba et al. |

(Continued)

FOREIGN PATENT DOCUMENTS

| | | |
|---|---|---|
| DE | 80 00 592 | 4/1980 |
| DE | 198 46 831 | 4/2000 |

(Continued)

OTHER PUBLICATIONS

Ying-Yu Tzou, et al., "FPGA-Based SVPWM Control IC for 3-Phase PWM Inverters" Proceedings of the 22$^{nd}$ International Conference on Industrial Electronics, Control and Instrumentation, Aug. 1996, pp. 138-143 (XP002360956).

(Continued)

*Primary Examiner* — Erick Glass
(74) *Attorney, Agent, or Firm* — Lipsitz & McAllister, LLC

(57) ABSTRACT

A surgical motor control device for controlling a surgical drive unit comprises a sensorless electric motor with M motor windings. The motor control device is configured to perform a method for controlling the drive unit. The motor control device be configured to control the drive unit using a multiphase PWM method.

An improved method for controlling a surgical drive unit and an improved surgical drive system are also proposed.

19 Claims, 8 Drawing Sheets

U.S. PATENT DOCUMENTS

| | | | |
|---|---|---|---|
| 5,994,867 A | 11/1999 | Birk et al. | |
| 6,013,991 A | 1/2000 | Philipp | |
| 6,014,323 A * | 1/2000 | Aiello et al. | 363/71 |
| 6,037,724 A | 3/2000 | Buss et al. | |
| 6,059,806 A | 5/2000 | Hoegerle | |
| 6,086,544 A | 7/2000 | Hibner et al. | |
| 6,101,109 A | 8/2000 | Duba et al. | |
| 6,118,932 A | 9/2000 | Maurio et al. | |
| 6,236,580 B1 * | 5/2001 | Aiello et al. | 363/37 |
| 6,249,094 B1 | 6/2001 | Zeh et al. | |
| 6,292,678 B1 | 9/2001 | Hall et al. | |
| 6,340,851 B1 | 1/2002 | Rinaldi et al. | |
| 6,643,149 B2 | 11/2003 | Arnet et al. | |
| 6,819,078 B2 | 11/2004 | Ho | |
| 6,885,163 B2 | 4/2005 | Heidrich | |
| 7,362,062 B2 | 4/2008 | Schneider et al. | |
| 7,422,582 B2 | 9/2008 | Malackowski et al. | |
| 7,514,890 B2 | 4/2009 | Schneider et al. | |
| 7,740,628 B2 | 6/2010 | Hoegerle et al. | |
| 2001/0029315 A1 | 10/2001 | Sakurai et al. | |
| 2002/0044472 A1 | 4/2002 | Arnet et al. | |
| 2002/0196115 A1 | 12/2002 | Yamakage et al. | |
| 2003/0155878 A1 | 8/2003 | Murai | |
| 2004/0071003 A1 | 4/2004 | Cocconi | |
| 2005/0123408 A1 | 6/2005 | Koehl | |
| 2006/0071541 A1 | 4/2006 | Berg | |
| 2006/0074405 A1 | 4/2006 | Malackowski et al. | |
| 2006/0119305 A1 | 6/2006 | Lee et al. | |
| 2007/0147806 A1 | 6/2007 | Schneider et al. | |
| 2007/0154192 A1 | 7/2007 | Schneider et al. | |
| 2007/0250098 A1 | 10/2007 | Malackowski et al. | |
| 2008/0077149 A1 | 3/2008 | Hoegerle | |
| 2008/0118234 A1 | 5/2008 | Schneider et al. | |
| 2009/0200971 A1 * | 8/2009 | Iwaji et al. | 318/400.11 |

FOREIGN PATENT DOCUMENTS

| | | |
|---|---|---|
| DE | 20 202 724 | 6/2002 |
| DE | 102 25 857 | 1/2004 |
| DE | 20 2004 006 724 | 7/2004 |
| DE | 20 2004 012 388 | 9/2004 |
| DE | 20 2004 012 389 | 9/2004 |
| DE | 10 2004 020 808 | 11/2005 |
| DE | 10 2004 062 580 | 3/2006 |
| DE | 20 2008 006 868 | 8/2008 |
| DE | 10 2007 039 764 | 12/2008 |
| EP | 1 009 096 | 6/2000 |
| JP | 6-304175 | 11/1994 |
| WO | 96/01521 | 1/1996 |
| WO | 97/50171 | 12/1997 |
| WO | 98/06338 | 2/1998 |
| WO | 03/013372 | 2/2003 |
| WO | 03/052919 | 6/2003 |
| WO | 2004/036755 | 4/2004 |
| WO | 2006/012990 | 2/2006 |

OTHER PUBLICATIONS

Felix Jenny/Dieter Wüest, "Steuerverfahren für selbstgeführte Stromrichter", 1995 vdf Hochschulverlag AG an der ETH Zürich and B.G. Teubner Stuttgart (10 pages).

* cited by examiner

US 8,493,009 B2

SURGICAL MOTOR CONTROL DEVICE, SURGICAL DRIVE SYSTEM AND METHOD FOR CONTROLLING A SURGICAL DRIVE UNIT

CROSS-REFERENCE TO RELATED APPLICATIONS

This application claims the benefit of German Patent Application No. 10 2009 018 143.1 filed on Apr. 8, 2009.

The present disclosure relates to the subject matter disclosed in German application number 10 2009 018 143.1 of Apr. 8, 2009, which is incorporated herein by reference in its entirety and for all purposes.

FIELD OF THE INVENTION

The present invention relates to a surgical motor control device generally, and more specifically to a surgical motor control device for controlling a surgical drive unit comprising a sensorless electric motor with M motor windings, the motor control device being configured to perform a method for controlling the drive unit.

The present invention further relates to a method for controlling a surgical drive unit generally, and more specifically to a method for controlling a surgical drive unit with a sensorless electric motor comprising a rotor and M motor windings.

The present invention also relates to a surgical drive system generally, and more specifically to a surgical drive system comprising at least one control device and at least one surgical drive unit connectable to and controllable by the control device and/or at least one surgical instrument comprising a surgical drive unit, the at least one drive unit comprising a sensorless electric motor with a rotor and M motor windings, the control device being configured to perform a method for controlling the drive unit.

BACKGROUND OF THE INVENTION

Surgical drive units of surgical drive systems, for example, of systems of the kind mentioned at the outset, are normally cleansed, i.e., cleaned and optionally sterilized, after use during a surgical procedure carried out on a patient. A problem which occurs in drive units as a result of cleaning and sterilization is corrosion of contacts. It has, therefore, already been proposed that preferably electronically commutated direct-current motors that are not equipped with sensors be provided for surgical drive units. The sensors, for example, Hall-effect sensors, primarily serve, in particular, in the case of low rotational speeds, to determine a position of the rotor of the electric motor, in order to be able to optimally supply it with current.

Furthermore, it is known to use a pulse width modulation method to supply the total of M motor windings of the electric motor with current, M being a natural number, greater than or equal to two. A disadvantage of this is that the ideal current supply curve for each motor winding, namely a sinusoidal curve, can only be approximately achieved in practice. In particular, limits are reached due to limited clock frequencies of available processors for generating the pulse width modulation signals (PWM signals).

An object of the present invention is, therefore, to so improve a surgical motor control device, a surgical drive system and a method for controlling a surgical drive unit that a current supply curve is prescribable for the motor windings of the drive unit, which is as ideal as possible.

SUMMARY OF THE INVENTION

In a first aspect of the invention, a surgical motor control device for controlling a surgical drive unit comprising a sensorless electric motor with M motor windings ($R_{MW\_1}, \ldots, R_{MW\_M}$) is configured to perform a method for controlling the drive unit. The motor control device is configured to control the drive unit using a multiphase PWM method.

In a second aspect of the invention, a method for controlling a surgical drive unit with a sensorless electric motor comprising a rotor and M motor windings is a multiphase PWM method.

In a third aspect of the invention, a surgical drive system comprises at least one control device and at least one surgical drive unit connectable to and controllable by the control device and/or at least one surgical instrument comprising a surgical drive unit. The at least one drive unit comprises a sensorless electric motor with a rotor and M motor windings. The control device is configured to control the drive unit using a method for controlling the drive unit. The method for controlling being a multiphase PWM method.

BRIEF DESCRIPTION OF THE DRAWING FIGURES

The foregoing summary and the following description may be better understood in conjunction with the drawing figures, of which:

DETAILED DESCRIPTION OF PREFERRED EMBODIMENTS OF THE INVENTION

Figure 1:
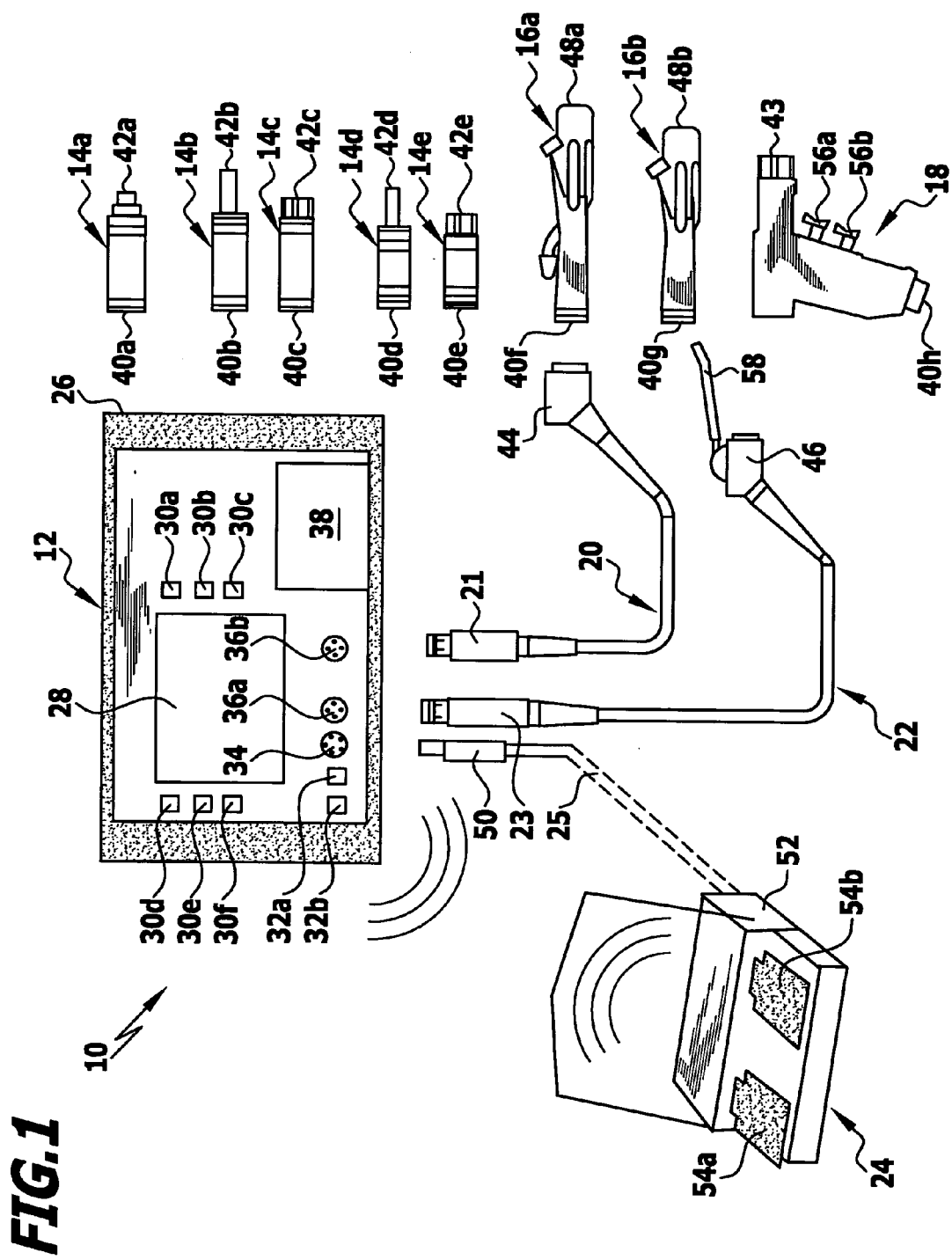
FIG. 1 is a schematic overall representation of a surgical drive system.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical motor control device for controlling a surgical drive unit comprising a sensorless electric motor with M motor windings ($R_{MW\_1}, \ldots, R_{MW\_M}$), the motor control device being configured to perform a method for controlling the drive unit, and the motor control device being configured to control the drive unit using a multiphase PWM method.

The device developed further in accordance with the invention enables control of the drive unit using multiphase PWM, i.e., each motor winding can, for example, be supplied with current by superimposition of two or more phases or subphases for generation of a pulse width modulation signal and the corresponding winding voltage. These subphases may, for example, all be clocked with the same clock frequency, but preferably somewhat phase-displaced relative to one another, so that a multiplication of the actual original clock frequency and, therefore, an even better approximation of the current supply curve to an ideal sinusoidal curve can be achieved. Furthermore, in particular, it is thus also possible to reduce electric losses of the motor, which are proportional to the square of the flowing current I, namely proportional $I^2 \cdot R$, where R is the resistance of the motor winding, by, for example, a reduction of voltage jumps generated by the pulse width modulation signals, at each motor winding. In particular, when motor control devices with relatively long control lines from the motor control device to the drive unit are used, an optimum current supply curve can thus be generated, even with relatively low clock frequencies of the pulse width modulation (PWM).

It is expedient for the motor control device to comprise a current supply device with which it is possible to supply each of the M motor windings sinusoidally or approximately sinusoidally with current. In particular, an almost ideal sinusoidal current supply curve can be generated by such a current supply device.

It is advantageous for the surgical motor control device to comprise a signal generating device with which a PWM signal is generatable for each of the M motor windings, and with which each of the M PWM signals is divisible into N subphase signals which are displaced in their phase position relative to one another through 360°/N in each case. By virtue of this special signal generating device, it is, in particular, possible, with a fixedly prescribed clock frequency, by generation of the N subphase signals displaced, in each case, through 360°/N, to achieve in total a multiplication of the available actual clock frequency by the factor N, N being the number of subphases and at least two. The generated current supply curve can thereby be adapted even more optimally to an ideal sinusoidal curve. Furthermore, it is thus possible, in spite of a prescribed limit of a maximum clock frequency in processors currently available on the market, to achieve even higher frequencies for the PWM. Also, owing to the increase in the clock frequency with the same current supply capacity, smaller voltage jumps can be achieved at the individual motor windings, whereby the power loss at each motor winding, caused by the so-called current ripple, can be reduced by the factor $1/N^2$. The overall efficiency of the motor control device is significantly increased. N and M define numbers of the aforementioned elements and devices, respectively, with N and M being at least two in each case.

Furthermore, in accordance with a preferred embodiment of the invention, a transducer device can be provided, with which the N subphase signals associated with a respective one of the M motor windings are convertible into N subphase winding voltages which are displaced in their phase position relative to one another through 360°/N in each case, with which in order to generate a current flow through each of the M motor windings it is possible to apply a winding voltage to each of the M motor windings, and with which it is possible to separately superimpose the N subphase winding voltages associated with a respective one of the M motor windings, for each of the M motor windings, for formation of the respective winding voltage that is applied to the respective motor winding in order to generate the winding current. By virtue of this special transducer device, it is possible to convert the phase-displaced subphase signals into corresponding subphase winding voltages, which are then superimposed separately for each motor winding for formation of the respective winding voltage.

The design of the surgical motor control device is particularly simple when the transducer device is so configured that the N subphase winding voltages, associated with a respective one of the M motor windings, are superimposable by addition.

In order to ensure in a simple way that on the basis of the generated subphase signals, a supply current curve is achievable, which, all in all, is as ideal as possible, it is expedient for the transducer device to be so configured that the N subphase winding voltages associated with a respective one of the M motor windings are generatable with the same respective signal amplitude.

It is advantageous for the transducer device to be so configured that the N subphase winding voltages associated with a respective one of the M motor windings are superimposable in such a way for formation of the respective winding voltage that a signal amplitude of the winding voltage is 1/N of a signal amplitude of the respective N subphase winding voltages. This means that the original voltage jumps, i.e., the signal amplitudes of the subphase winding voltages, are greater by the factor N than the signal amplitude of the winding voltage at the respective motor winding. All in all, the power loss at the motor winding caused by the current ripple can also be reduced by the factor $1/N^2$ by this reduction in the voltage jumps by the factor 1/N.

The motor control device advantageously comprises N*M amplifier circuits which are controllable with each of the N subphase signals associated with a respective one of the M motor windings. In this way, the individual subphase signals are convertible independently of one another into subphase winding voltages. Required switching times of the amplifier circuits are then based on the respective clock frequency of the entire system and not on the higher clock frequency generated by superimposition of the subphase winding voltages. N*M is the product of the number N of subphase signals and the number M of motor windings.

To enable superimposition of the total of M*N subphase winding voltages for formation of the M winding voltages, it is expedient for a total of M multiphase transmission devices to be provided for superimposing the M*N subphase winding voltages for formation of the winding voltages. It is thus possible to associate with each motor winding a multiphase transmission device by means of which the winding voltage is superimposed from the respective N subphase winding voltages for each motor winding.

The design of the surgical motor control device is particularly simple when the M multiphase transmission devices are in the form of multiphase transformers.

In particular, the manufacture and design of the multiphase transmission devices can be simplified by each of the M multiphase transmission devices comprising N single phase transmission devices. With the N single phase transmission devices, where these are appropriately interconnected, the N subphase winding voltages can be superimposed for formation of the respective winding voltage for each motor winding.

Each single phase transmission device is preferably in the form of a single transformer. In particular, this makes it possible to use conventional single transformers with primary and secondary coils as single phase transmission devices and to interconnect these to a multiphase transmission device.

In accordance with a further preferred embodiment of the invention, it can be provided that each of the N single transformers of one of the M multiphase transmission devices comprises a primary coil with a primary input and a primary output and a secondary coil inductively coupled to the primary coil with a secondary input and a secondary output, and that each primary output of one of the N primary coils is electrically conductively connected to a secondary output of a secondary coil of another one of the N single transformers of the same multiphase transmission device. With this form of interconnection of the N single transformers to form a multiphase transmission device, the subphase winding voltages can be automatically added and the sum simultaneously divided by the number N of subphase signals. This does not require an elaborate calculating unit. In particular, the connecting of the single transformers is not to take place in pairs, but permuted, i.e., by corresponding permutation of the primary outputs and the secondary outputs of the single transformers.

To enable coupling of the subphase signal voltages in a simple way into the multiphase transmission device, it is advantageous for each primary input of each of the N primary coils of a multiphase transmission device to be electrically conductively connected to one of the N amplifier circuits which are associated with each of the M multiphase transmission devices. Each subphase winding voltage can thus be coupled into one of the N single phase transmission devices of each multiphase transmission device.

Each secondary input of each of the N secondary coils of a multiphase transmission device is advantageously electrically conductively connectable to the associated common motor winding. This can be effected by a fixedly installed electrically conductive connection, for example, a permanently installed connection cable or by a connection cable detachably connectable to the motor control device and the drive unit.

The design of the multiphase transmission device is particularly simple when the single phase transmission devices are connected in the shape of a star, so that the primary circuit of each single phase transmission device is connected in series in each case with the secondary circuit of the next single phase transmission device. In particular, the desired superimposition of the subphase winding voltages can thus be ensured in a simple way by addition.

Preferably, N=2, 3, 4, 5 or 6 and/or M=2, 3, 4, 5 or 6. This means that the PWM signals are multiplied by the factor N, i.e., doubled, tripled, quadrupled, quintupled or sextupled. Optionally, M=2, 3, 4, 5 or 6 motor windings can be provided, which can be supplied with current. Of course, the numbers N and M can, in principle, be any natural number greater than 1.

It is expedient for the surgical motor control device to comprise a digital signal processor for generating the PWM signals for each motor winding. In particular, a single digital signal processor can be provided for generating all PWM signals for the total of M motor windings.

It is particularly expedient for a controller to be provided for controlling the digital signal processor and/or a freely programmable integrated circuit. In particular, the freely programmable integrated circuit can be a field programmable gate array (FPGA).

In accordance with a further preferred embodiment of the invention, the surgical motor control device can further comprise a clock generator device for prescribing a PWM clock frequency for performing the PWM method. The clock frequency or basic clock frequency of the PWM method can thus be prescribed in a specific manner with the clock generator device.

The signal generating device preferably interacts in such a way with the clock generator device that the N subphase signals are generatable in each case with the PWM clock frequency. In particular, it can thereby be ensured that none of the N subphase signals is generated with a clock frequency other than the PWM clock frequency. A phase shift or a phase displacement of the subphase signals can be effected, for example, by a delay device which divides the period of the PWM clock frequency into N equal parts.

It is expedient for the clock generator device to be configured to generate PWM clock frequencies ranging from 50 kHz to 500 kHz. Preferably, the PWM clock frequency ranges from 10 kHz to 1000 kHz. It is expedient for it to be 100 kHz.

It is advantageous for the digital signal processor to be configured to modulate a pulse width of the PWM signal for generating a sinusoidal curve of the winding voltages. By corresponding modulation, i.e., prescribing the pulse widths of the PWM signals, correspondingly long signal voltage pulses can thus be generated, on the basis of which corresponding currents flow within a prescribed time unit and generate the current supply curve.

In accordance with a further preferred embodiment of the invention, a rotor position determining device can also be provided for determining a rotor position of the electric motor in order to control a supplying of current to the M motor windings. In particular, such a rotor position determining device can also be provided in a surgical motor control device of the kind described at the outset. It makes it possible to determine a rotor position of the electric motor in order to optimize, in dependence upon its position, a supplying of current to the M motor windings, i.e., to accelerate or brake the rotor in a specific manner or to allow it to rotate further at a constant rotational speed.

In particular, the surgical motor control device can do without sensors on the electric motor when the rotor position determining device comprises a current supply interruption device with which at least one of the M motor windings is separable from a power supply of the drive unit for a time interval $t_{interrupt}$ in order to determine a position of a rotor of the electric motor, when the counter-electromotive force in at least one of the M motor windings is measurable with the rotor position determining device during the time interval $t_{interrupt}$, and when the rotor position determining device comprises a calculating unit for calculating an actual position of the rotor from the measured counter-electromotive force. A rotor position can be calculated in simple way from the size and orientation of the counter-electromotive force, i.e., the voltage induced in the motor winding separated from the current supply.

It is advantageous for the current supply interruption device to be so configured that all motor windings are simultaneously separable from the power supply of the drive unit for the time interval $t_{interrupt}$. In particular, it is thus possible to simultaneously determine the counter-electromotive force for not only one, but two or also more motor windings, in order to able to clearly identify the rotor position. Furthermore, in the case of simultaneous interruption of the current supply, interference signals from the other motor windings which continue to be supplied with current can be avoided.

The design of the current supply interruption device is particularly simple when it is so configured that a constant value is prescribable for the time interval $t_{interrupt}$. Optionally, it is also conceivable to alter the time interval $t_{interrupt}$, for example, in dependence upon a rotational speed of the electric motor, such that the time interval $t_{interrupt}$ is shortened when the rotational speed of the electric motor increases, and vice versa.

The current supply interruption device is preferably so configured that after measurement of the counter-electromotive force all motor windings are electrically conductively connectable again to the power supply of the drive unit. In this way, an intervention in the supplying of current to the electric motor can be minimized, namely limited to the interruption thereof for measurement of the counter-electromotive force, as the motor windings are only separated from the power supply during the measuring of the counter-electromotive force. Aside from that, the motor windings can be supplied with current in the desired manner.

In order not to excessively influence the current supply curve, it is advantageous for the rotor position determining device to be so configured that the counter-electromotive force is only measurable when the motor current of at least one of the M motor windings has dropped to zero. This makes it possible to provide the time interval $t_{interrupt}$ during which the counter-electromotive force is measured in an area of the current supply curve in which only small amplitudes are realized.

It is expedient for the rotor position determining device to be so configured that a total of $N_{total}=N*M$ measurements of the counter-electromotive force are performable per rotor revolution. In particular, at the zero crossings of all subphases the current supply to the motor windings can thus be interrupted in order to determine the counter-electromotive force. This allows a particularly high accuracy when determining the counter-electromotive force, in particular, at low rotational speeds.

In accordance with a further preferred embodiment of the invention, it can be provided that the rotor position determining device is so configured that the measurement of the counter-electromotive force at one of the M motor windings is performable in a time interval $t_M \pm \Delta t$, the voltage applied to the motor winding being zero at the point in time $t_M$. In particular, the value for $\Delta t$ is alterable in dependence upon the PWM clock frequency. In this way, interferences during the switching-off of the individual motor windings, i.e., when separating these from the power supply, can be avoided as far as possible, as only low effective voltages have to be switched to zero.

The transducer device preferably comprises M final stage power circuits for supplying current to the M or at least two motor windings of the drive unit. A final stage power circuit can thus be provided for each motor winding of the drive unit. In particular, each final stage power circuit can comprise N amplifier circuits for amplifying the N subphase signals.

It is advantageous for the surgical motor control device to comprise M FET driver circuits, one FET driver circuit being associated with each final stage power circuit. The FET driver circuits preferably comprise corresponding driver stages for each amplifier circuit of the final stage power circuits in order to convert the subphase signals into subphase winding voltages.

In accordance with a further preferred embodiment of the invention, it can be provided that the signal generating device comprises a freely programmable integrated circuit which is associated, on the one hand, with the digital signal processor and, on the other hand, with the M FET driver circuits. In particular, the freely programmable integrated circuit can be configured to convert or break the PWM signals down into N subphase signals.

The invention further relates to a method for controlling a surgical drive unit with a sensorless electric motor comprising a rotor and M motor windings, the method being a multiphase PWM method.

The controlling of a surgical drive unit with a sensorless electric motor using a multiphase PWM method makes it possible, on the one hand, to obtain current supply curves of the motor windings, ideally each in the form of a sinusoidal curve, and, on the other hand, by virtue of the more ideal current supply curves, to reduce an electric power loss, more specifically, in the manner described hereinabove.

To minimize the electric power loss and achieve optimized operation of the electric motor, it is expedient for each of the M motor windings to be sinusoidally or approximately sinusoidally supplied with current using the multiphase PWM method.

Preferably, a PWM signal is generated for each of the M motor windings, and each of the M PWM signals is divided to N subphase signals, which are displaced in their phase position relative to one another through 360°/N in each case. This makes it possible, in a simple way, to increase, all in all, a prescribed clock frequency of the PWM signal at the motor windings by the factor N, the N subphase signals being clocked in each case only with a clock frequency of the PWM signal.

It is advantageous for the N subphase signals associated with a respective one of the M motor windings to be converted into N subphase winding voltages which are displaced in their phase position relative to one another through 360°/N in each case, for a winding voltage to be applied to each of the M motor windings in order to generate a current flow through each of the M motor windings, and for the N subphase winding voltages associated with a respective one of the M motor windings to be separately superimposed, for each of the M motor windings, for formation of the respective winding voltage that is applied to the respective motor winding in order to generate the winding current. The method thus developed further makes it possible to generate the subphase signals with a relatively low clock frequency, to convert the subphase signals into subphase winding voltages and to subsequently superimpose the subphase winding voltages for formation of the winding voltage for each of the motor windings.

The method is particularly easy to perform when the subphase winding voltages associated with a respective one of the M motor windings are superimposed by addition.

It is expedient for the N subphase winding voltages associated with a respective one of the M motor windings to all have the same signal amplitude. They can thus be superimposed in a simple way, for example, by addition.

It is advantageous for the N subphase winding voltages associated with a respective one of the M motor windings to be superimposed in such a way for formation of the respective winding voltage that a signal amplitude of the winding voltage is 1/N of a signal amplitude of the respective N subphase winding voltages. In this way, the electric power loss caused by the current ripple owing to the current supply can be reduced by $1/N^2$.

Preferably, an amplifier circuit is controlled with each of the N subphase signals associated with a respective one of the M motor windings. This makes is possible to use amplifier circuits which are operable at relatively low clock frequencies which are currently available on the market.

It is expedient for the total of M*N subphase winding voltages to be superimposed by means of M multiphase transmission devices for formation of the winding voltages. It is thus possible to associate with each motor winding a multiphase transmission device with which the subphase winding voltages associated with the respective motor winding are superimposed for formation of the respective winding voltage.

In particular, performance of the method is further simplified by multiphase transformers being used as multiphase transmission devices.

Preferably, M multiphase transmission devices each with N single phase transmission devices are used. With these, the M*N subphase winding voltages can be converted in a simple way to the M winding voltages.

It is advantageous for single transformers to be used as single phase transmission devices. In particular, these can be interconnected in a desired manner.

To superimpose the subphase winding voltages in a simple way, for example, by addition, it is advantageous for each of the N single transformers of one of the M multiphase transmission devices to comprise a primary coil with a primary input and a primary output and a secondary coil inductively coupled to the primary coil with a secondary input and a secondary output, and for each primary output of one of the N primary coils to be connected to a secondary output of a secondary coil of another one of the N single transformers of the same multiphase transmission device.

It is expedient for each primary input of each of the N primary coils of a multiphase transmission device to be connected to one of the N amplifier circuits which are associated with each of the M multiphase transmission devices. In this way, the N subphase winding voltages which are applied to a respective output of the N amplifier circuits can be coupled in a desired manner into the multiphase transmission device for superimposition.

To enable the winding voltages generated by superimposition to be applied to the respective motor windings, it is advantageous for each secondary input of each of the N secondary coils of a multiphase transmission device to be connected to the associated common motor winding.

Advantageously, the single phase transmission devices are connected in the shape of a star, so that the primary circuit of each single phase transmission device is connected in series in each case with the secondary circuit of the respective next single phase transmission device. In particular, a superimposition of the subphase winding voltages by addition with simultaneous division of the superimposed voltage by the factor N can thus be achieved.

Expediently, N=2, 3, 4, 5 or 6 and/or M=2, 3, 4, 5 or 6. It is also conceivable to provide number values for N and M which are greater than 6; the method is preferably performed with N=3 and M=3. A clock frequency can thus be virtually tripled by the factor N=3. M=3 means that 3 motor windings are provided on an electric motor, and the above-described devices associated with the motor windings for performing the method are also provided in threes.

The PWM signals for each motor winding can be generated in a simple way with a digital signal processor.

It is expedient for the digital signal processor to be controlled by a controller circuit. For example, the signal processor can prescribe a clock frequency for the method.

Expediently, the PWM method is performed with a PWM clock frequency. This can be prescribed by the controller and/or the digital signal processor. The PWM frequency is a basic frequency of the method, which is multipliable by the factor N by division of the PWM signal into subphase signals, although all calculations for each subphase need only be carried out for the PWM clock frequency in each case.

Preferably, the N subphase signals are generated with the PWM clock frequency. This makes it possible to perform the method with processors available on the market, in spite of an increased superimposed frequency of the subphase signals.

It is advantageous for a frequency ranging from 10 kHz to 1000 kHz to be used as PWM clock frequency. Rotational speeds of electric motors of 100,000 revolutions per minute can be readily achieved with such PWM clock frequencies, with the generated current supply curve being very approximate to an ideal sinusoidal curve. Advantageously, the PWM clock frequency ranges from 50 kHz to 500 kHz; it preferably ranges from 100 kHz to 300 kHz. Expediently, the PWM clock frequency is 200 kHz. In particular, electronic processors are available on the market for such clock frequencies.

In particular, in order to generate a sinusoidal curve of the winding voltages, it is advantageous for a pulse width of the PWM signal to be correspondingly modulated.

Furthermore, it is advantageous, in particular, also in a method of the kind described at the outset, for a rotor position of the electric motor to be determined in order to control a supplying of current to the M motor windings. It can thus be ensured that the electric motor can be accelerated or braked in a desired manner or operated at a constant rotational speed.

In order to determine a position of a rotor of the electric motor, it is expedient for at least one of the M motor windings to be separated from a power supply of the drive unit for a time interval $t_{interrupt}$, for the counter-electromotive force in at least one of the M motor windings to be measured during the time interval $t_{interrupt}$, and for an actual position of the rotor to be calculated from the measured counter-electromotive force. The thus further developed method according to the invention enables determination of a rotor position without the aid of sensors. The rotor position is calculated from a counter-electromotive force measured during the time interval $t_{interrupt}$, i.e., from the voltage induced in a currentless motor winding. An actual position of the rotor can thus be clearly determined, and a supplying of the electric motor with current can be optimized on the basis of the determined actual position of the rotor.

To minimize interference signals in the determining of the counter-electromotive force, it is advantageous for all motor windings to be simultaneously separated from the power supply of the drive unit for the time interval $t_{interrupt}$.

The method can be performed in a particularly simple way when a constant value is prescribed for the time interval $t_{interrupt}$. It may, of course, also be expedient for the time interval $t_{interrupt}$ to be adaptable, more specifically, for example, in dependence upon a rotational speed of the motor. For example, it is conceivable to shorten the time interval $t_{interrupt}$ all the more, the quicker the rotor of the electric motor rotates.

In order to intervene as little as possible in the supplying of the electric motor with current, it is advantageous for all motor windings to be connected again to the power supply of the drive unit after measurement of the counter-electromotive force.

In order that interference signals can be further minimized, it is expedient for the counter-electromotive force to only be measured when the motor current of at least one of the M motor windings has dropped to zero. In addition, large voltage differences when separating the respective motor winding or motor windings from the power supply unit can thus be prevented.

In particular, a particularly accurate determination of the rotor position can be achieved by N*M measurements of the counter-electromotive force being performed per rotor revolution. In particular, the method can thus be performed in such a way that at each zero crossing of a subphase the counter-electromotive force in the respective motor winding is measured and the rotor position calculated accordingly.

It is expedient for the measurement of the counter-electromotive force at one of the M motor windings to be performed in a time interval $t_M \pm \Delta t$, the point in time $t_M$ being so selected that the motor voltage applied to the motor winding at the point in time $t_M$ is zero. This variant of the method makes use of the fact that per revolution of the rotor each generated current or voltage curve at each motor winding has at least 2 zero crossings and a voltage difference when separating the motor winding from the power supply unit is particularly small in the region of a zero crossing. In particular, interference signals which might negatively influence the determining of the counter-electromotive force can thus be minimized or even eliminated.

The invention further relates to a urgical drive system comprising at least one control device and at least one surgical drive unit connectable to and controllable by the control device and/or at least one surgical instrument comprising a surgical drive unit, the at least one drive unit comprising a sensorless electric motor with a rotor and M motor windings, the control device being configured to control the drive unit using a method for controlling the drive unit, the method for controlling being a multiphase PWM method In particular, with such a multiphase PWM method, electric power losses can be minimized and, at the same time, as described hereinabove, almost ideal current supply curves can be achieved for the motor windings of the drive unit.

It is expedient for the control device to be in the form of one of the above-described motor control devices. The surgical drive system then also has the advantages described hereinabove in connection with preferred embodiments of the motor control device.

Furthermore, it is expedient for the control device to be configured to control the drive unit using one of the above-described methods for controlling the drive unit. The surgical drive system thus also has the advantages described hereinabove in connection with the variants of the method according to the invention.

The following description of preferred embodiments of the invention serves to provide a more detailed explanation in conjunction with the drawings.

FIG. 1 shows schematically a surgical drive system generally designated by reference numeral 10, comprising a control device in the form of a control unit 12, five drive units 14a to 14e, two shaver handpieces 16a and 16b also forming drive units, a pistol handpiece 18 forming a further drive unit, two connection cables 20 and 22 and a foot control unit 24.

The control unit 12 comprises a flat screen 28 in the form of a touch screen arranged in a housing 26. Arranged on either side of the screen 28 are three operating elements 30a to 30c and 30d to 30f, respectively.

Two switches 32a and 32b are arranged below the screen 28 on a line with a connection socket 34 for connection of the foot control unit 24 via an optional connection cable 25 and with two connection sockets 36a and 36b for connection of the connection cables 20 and 22, with which the drive units can be connected to the control unit 12. Optionally, it is also possible to provide a connection 38 for a fluid system for supplying fluids to and removing fluids from an operating site and, for example, also for serving flush or exhaust ducts on handpieces or tools, not shown, which are connectable to the drive units 14, the shaver handpieces 16 or the pistol handpiece 18, and together with which the drive units form surgical instruments of the drive system 10.

The drive units 14a to 14e each comprise a cable coupling 40a to 40e. These are optionally connectable to a coupling part 44 of the connection cable 20 or to a coupling part 46 of the connection cable 22. Similarly, the two shaver handpieces 16a and 16b and the pistol handpiece 18 each comprise a cable coupling 40f, 40g and 40h, respectively. These are connectable to one of the two coupling parts 44 or 46.

At their respective other end, the drive units 14a to 14e are equipped with handpiece or tool couplings 42a to 42e to which handpieces, not shown, for example, drill handpieces, saw handpieces or the like, can be coupled and driven by the drive units 14a to 14e. Depending on their configuration, the drive units 14a to 14e can also be directly fitted with tools, not shown, such as, for example, drills or saw blades, in order to form surgical instruments.

The drive units are preferably of sensorless configuration, i.e., they have no sensors for determining a rotational speed of the drive units during operation. The drive units of the drive system 10 differ not only, as shown schematically in FIG. 1, externally, but also with respect to their internal design. This means that the motors installed in the drive units can be of a different type and vary, for example, in their characteristics such as, for example, minimum rotational speed, maximum rotational speed, maximum current and maximum torque. Furthermore, as in the two shaver handpieces 16a and 16b, gearings may be integrated, which, optionally, may also be integrated in handpieces which can be coupled to the drive units 14 and to the pistol handpiece 18. Depending on their configuration, the handpieces themselves may also be additionally fitted with different instrument tips in the form of surgical tools.

Furthermore, the shaver handpieces 16a and 16b each comprise a shaver coupling 48a and 48b, respectively, for connection of a shaver, for example, for use in arthroscopy.

For connection to the control unit, the connection cables 20 and 22 are provided with couplings 21 and 23, via which they are connectable to the connection sockets 36a and 36b.

The foot control unit 24 is connected via a wireless data transmission device to the control unit 12, for example, via an infrared or radio transmission system. Optionally, connection of the foot control unit 24 is also possible via a coupling part 50 of the connection cable 25, which is connectable to the connection socket 34. Arranged on a housing 52 of the foot control unit 24 are two foot-operable switches 54a and 54b, via which, in particular, an anticlockwise rotation and a clockwise rotation, respectively, of the drive units can be controlled.

The pistol handpiece 18 is equipped with two encoders 56, with encoder 56a being provided, for example, for activating clockwise motor rotation, and encoder 56b for activating anticlockwise motor rotation.

The connection cables 20 and 22 differ in that differently from connection cable 20, there is provided on connection cable 22 an actuating lever 58 with which an operator can activate motor operation of a drive unit 14, a shaver handpiece 16 or the pistol handpiece 18.

Figure 2:
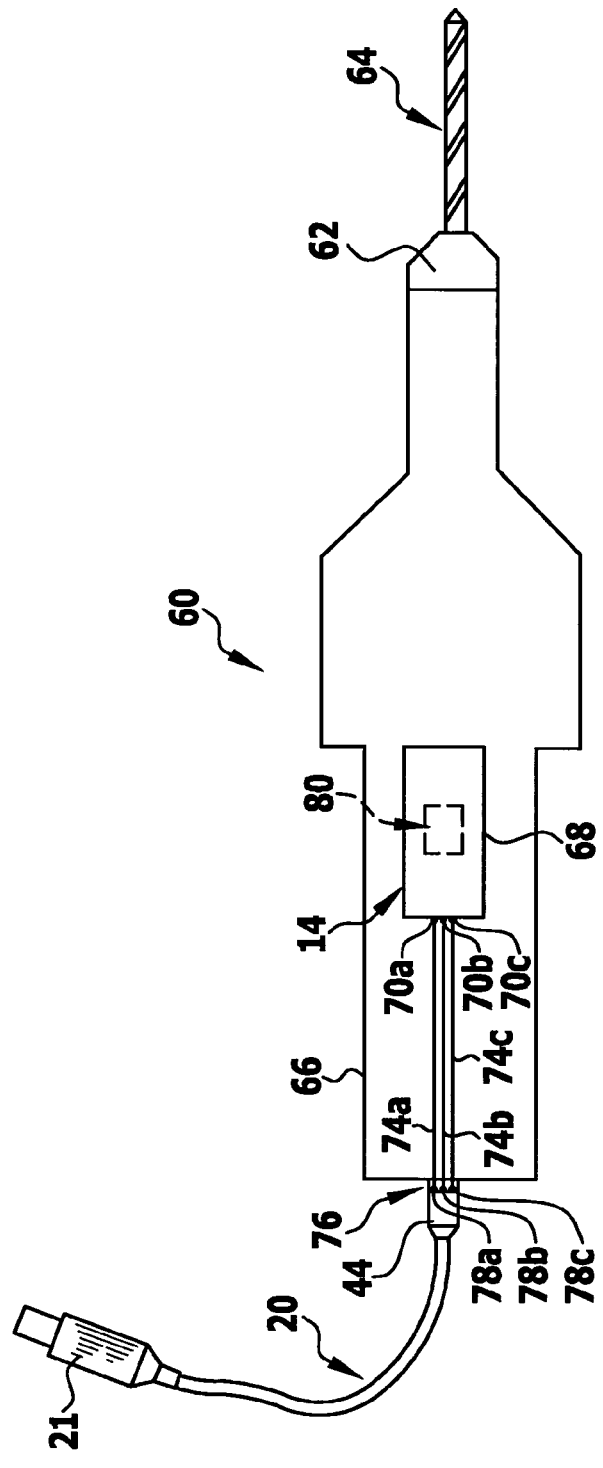
FIG. 2 is a schematic representation of a surgical instrument and a control device of a surgical drive system.

FIG. 2 shows schematically the design of a surgical instrument 60. It comprises a drive unit 14, for example, a drive unit 14a to 14e, and a tool 64, for example, in the form of a drill shown in FIG. 2, which is connectable to a coupling 62 at the distal end.

Arranged in a housing 66 of the drive unit 14 is a motor 68 comprising three connection contacts 70a, 70b and 70c which are each connected to two of a total of three motor windings 72a, 72b and 72c. The connection contact 70a is connected to the motor windings 72b and 72c, the connection contact 70b to the motor windings 72a and 72b, and the connection contact 70c to the motor windings 72a and 72c.

The connection contacts 70a, 70b and 70c are connected by means of connection lines 74a, 74b and 74c to a coupling element 76 arranged at the proximal end, more specifically, to its connection contacts 78a, 78b and 78c. The coupling element 76 is configured so as to correspond to the coupling part 44 of the connection cable 20 for connection thereto.

The connection cable 20 itself is a three-conductor connection cable with three single conductors 20a, 20b and 20c. In the embodiment shown in FIG. 2, no control or data lines are provided on the connection cable 20 or on the drive unit 14.

Furthermore, a motor identification device 80 such as is known, for example, from DE 20 2008 006 868 U1 is optionally integrated into the motor 68.

The control unit 12 comprises a motor control device 82 which is arranged in the housing 26 and, for reasons of simplicity, will be referred to hereinbelow as control device 82. The motor 68 which generally comprises M motor windings, also referred to as $R_{MW\_1}$, $R_{MW\_M}$, can be controlled by the control device 82. In the embodiment described hereinbelow, the number M of motor windings is three, and the motor windings are designated by 72a, 72b and 72c.

The control device comprises a controller 84, which is interconnected to a digital signal processor 86. The digital signal processor 86 is, in turn, coupled to a freely programmable integrated circuit 88 in the form of an FPGA. This serves to control three FET driver circuits 90a, 90b and 90c. The FET driver circuits 90a, 90b and 90c are each connected to an final stage power circuit 92a, 92b and 92c, which each comprise three identical amplifier circuits 94a, 94b and 94c. For supplying power to the control device 82 or to the drive system 10, a power supply 96 is provided, which makes the necessary supply voltages available to all circuits and elements of the control device 82.

Figure 6:
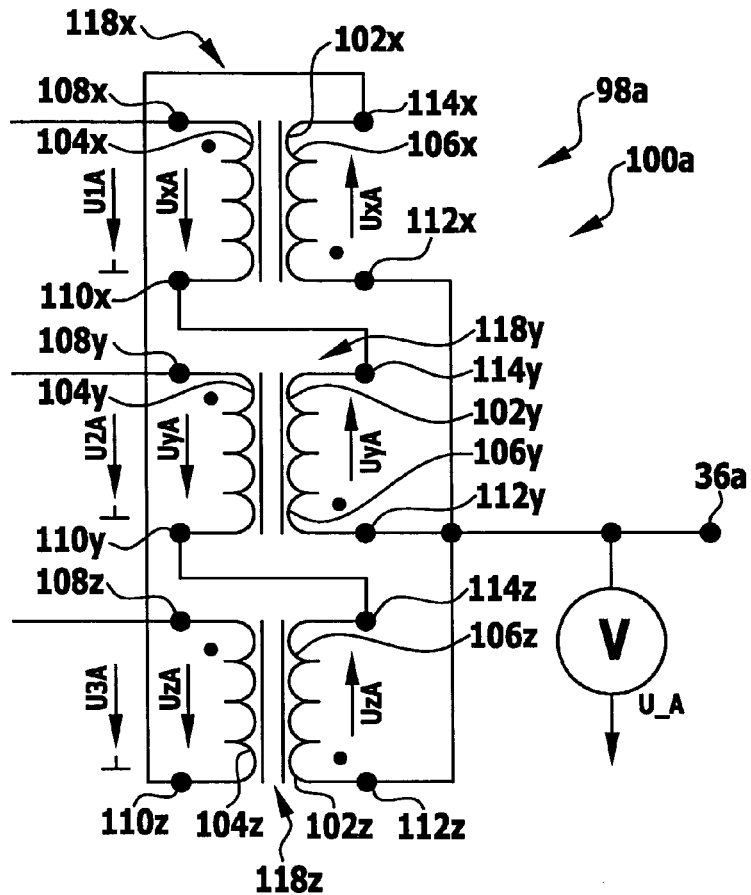
FIG. 6 is a schematic representation of a multiphase transmission device for a motor winding.

Each final stage circuit 92a, 92b and 92c is interconnected to an associated multiphase transmission device 98a, 98b and 98c, which is in the form of a multiphase transformer 100a, 100b and 100c respectively. The multiphase transformers 100a, 100b and 100c are all of identical design and are explained, by way of example, in greater detail hereinbelow with reference to the multiphase transformer 100a in conjunction with FIG. 6.

The multiphase transformer 100a comprises three single transformers 102x, 102y and 102z. These are each formed by two coils inductively coupled to each other, namely a primary coil 104x, 104y and 104z and a secondary coil 106x, 106y and 106z, respectively. Each primary coil 104x, 104y and 104z comprises a primary input 108x, 108y and 108z and a primary output 110x, 110y and 110z. Furthermore, each secondary coil 106x, 106y and 106z comprises a secondary input 112x, 112y and 112z and a secondary output 114x, 114y and 114z.

Each of the primary inputs 108x, 108y and 108z is electrically conductively connected to a respective output of one of the three amplifier circuits 94a. The three secondary inputs 112x, 112y and 112z are electrically conductively connected to one another and to a connection contact 116a of the connection socket 36a, which also comprises two further connection contacts 116b and 116c, which are connected in an analog manner to the multiphase transformers 100b and 100c. The primary output 110x is electrically conductively connected to the secondary output 114y, the primary output 110y to the secondary output 114z, and the primary output 110z to the secondary output 114x. In this way, the single transformers 102x, 102y and 102z defining single-phase transmission devices 118x, 118y and 118z are connected in the shape of a star, so that the primary coil 104x, 104y, and 104z, also referred to as primary circuit, of each single-phase transmission device 118x, 118y and 118z is connected in series, in each case, with the secondary coil 106x, 106y and 106z, also referred to as secondary circuit, of the respective next single-phase transmission device 118y, 118z and 118x.

The single transformers 102x, 102y and 102z are therefore so connected that $$U\_A = \tfrac{1}{3}U1A + \tfrac{1}{3}U2A + \tfrac{1}{3}U3A$$

applies for their output voltages UxA, UyA and UzA in dependence upon the three input signals U1A, U2A and U3A, which are present at the primary inputs 108x, 108y and 108z.

Figure 4:
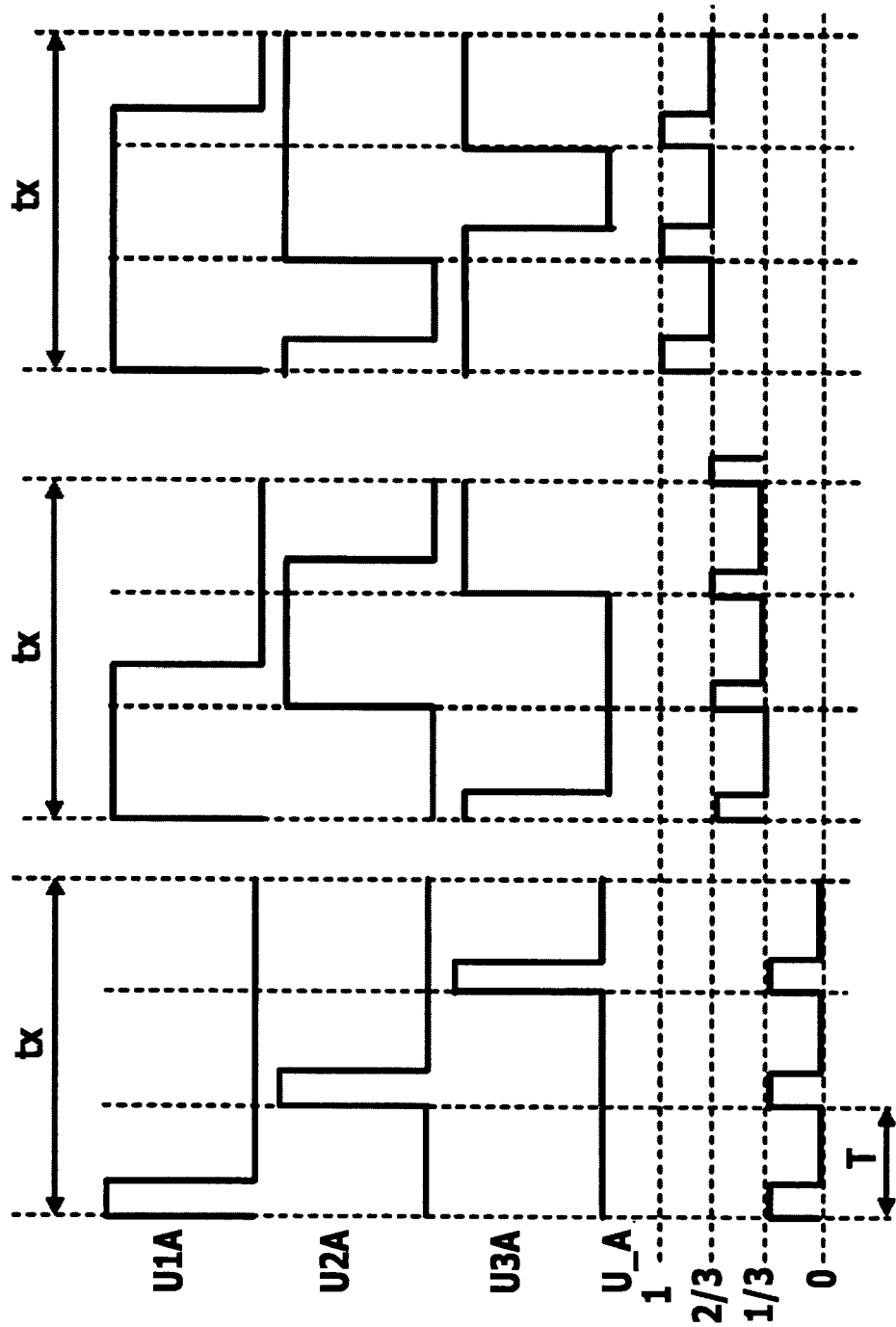
FIG. 4 is a schematic representation of the superimposition of subphase winding voltages for formation of winding voltages for three different pulse widths.

This superimposition of the input signals U1A, U2A, U3A, U1B, U2B, U3B, U1C, U2C and U3C, i.e., of the subphase winding voltages, generally represented as $U_{MW\_1\_1}, \ldots, U_{MW\_1\_N}, \ldots, U_{MW\_M\_1}, \ldots, U_{MW\_M\_N}$, is shown, by way of example, in FIG. 4 for three different pulse widths of the input signals. The period length $t_x$ shown in FIG. 4 is calculated from a clock frequency $f_{PWM}$ of the performed PWM method with $t_x = 1/f_{PWM}$.

A clock generator device, generally designated by reference numeral 132, of the control device 82 serves to prescribe the PWM clock frequency $f_{PWM}$ for performing the PWM method. The clock generator device comprises the controller 84 and the digital signal processor 86. The clock generator device 132 and the signal generating device 120 interact in the control device 82 in such a way that the subphase signals, generally designated by $S_{PWM\_1\_1}, \ldots, S_{PWM\_1\_N}, \ldots; S_{PWM\_M\_1}, \ldots, S_{PWM\_M\_N}$, can be generated with the PWM clock frequency $f_{PWM}$. The clock generator device 132 preferably generates a PWM clock frequency of 100 kHz.

The digital signal processor 86 forms a signal generating device 120, with which a PWM signal $S_{PWM\_1}, \ldots, S_{PWM\_M}$ can be generated for each of the M=3 motor windings $R_{MW\_1}, \ldots, R_{MW\_M}$, and with which each of the PWM signals $S_{PWM\_1}, \ldots, S_{PWM\_M}$ can be divided into N subphase signals $S_{PWM\_1\_1}, \ldots, S_{PWM\_1\_N}, \ldots, S_{PWM\_M\_1}, \ldots, S_{PWM\_M\_N}$, which are displaced relative to one another in their phase position through 360°/N, in each case, in the described embodiment with N=3, i.e., through 120°. The signal generating device 120 further comprises the circuit 88, which displaces the phase position of the individual subphase signals through 120° relative to one another, and the FET driver circuits 90a, 90b and 90c.

Figure 3:
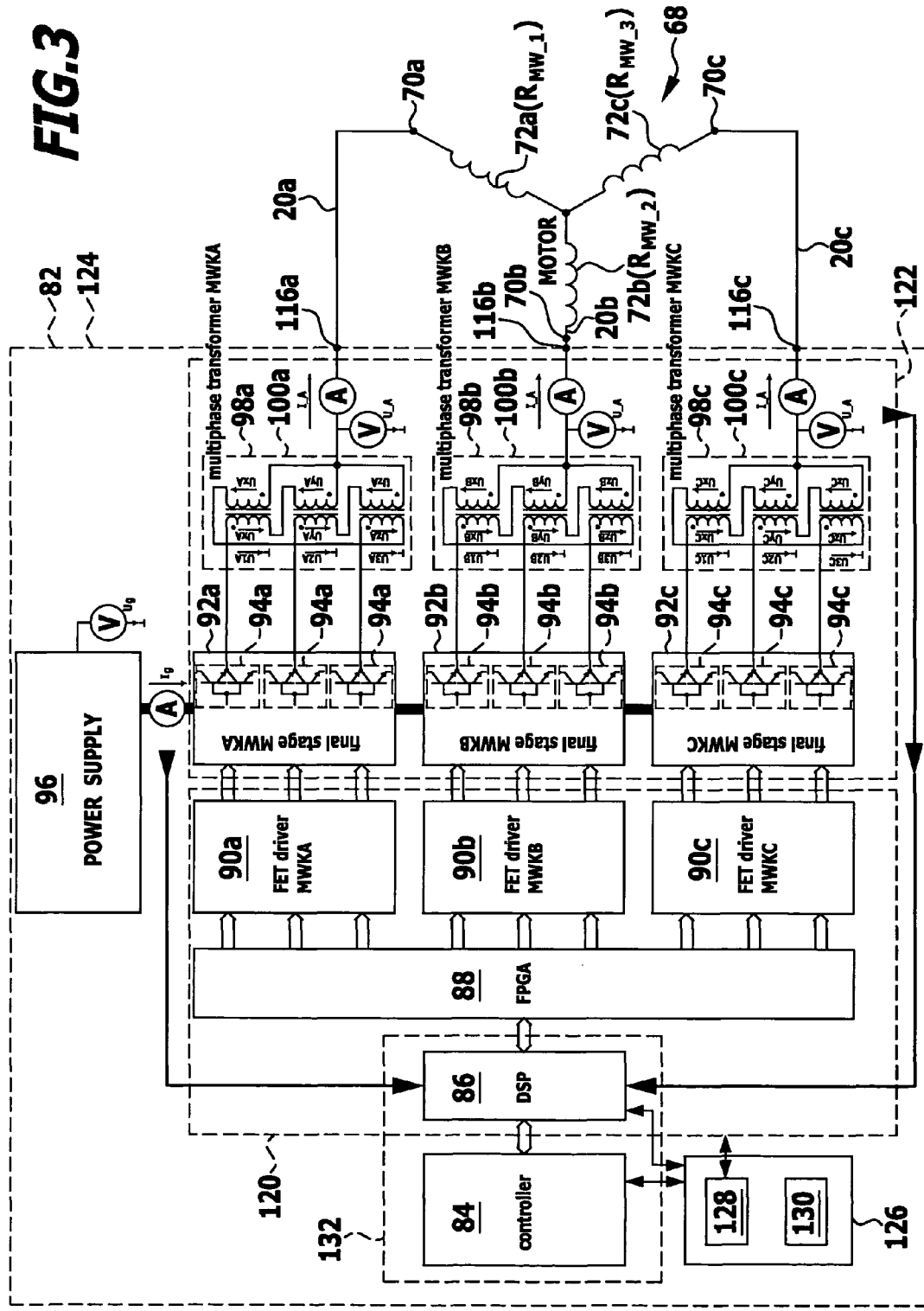
FIG. 3 is a partly block diagram-type representation of a motor control device for controlling a motor.

The control device 82 further comprises a transducer device 122, with which transducer device 122 the N subphase signals, associated with a respective one of the M=3 motor windings 72a, 72b and 72c, can be converted into N subphase winding voltages $U_{MW\_1\_1}, \ldots, U_{MW\_1\_N}; \ldots; U_{MW\_M\_1}, \ldots, U_{MW\_M\_N}$ which are displaced relative to one another in their phase position through 360°/N, in each case, i.e., with N=3, through 120°, with which transducer device 122, in order to generate a flow of current $I_{MW\_1}, \ldots, I_{MW\_M}$ through each of the M=3 motor windings $R_{MW\_1}, \ldots, R_{MW\_M}$, a winding voltage $U_{MW\_1}, \ldots, U_{MW\_M}$, shown in FIG. 3 as U_A, U_B and U_C, can be applied, and with which transducer device 122 the N subphase winding voltages, associated with a respective one of the M=3 motor windings, for each of the M motor windings, can be separately superimposed for formation of the respective winding voltage that is applied to the respective motor winding in order to generate the winding current $I_{MW\_1}, \ldots, I_{MW\_M}$, shown in FIG. 3 as I_A, I_B and I_C. The transducer device 122 comprises the final stage power circuits 92a, 92b and 92c and the multiphase transmission devices 98a, 98b and 98c. Owing to this configuration and the circuitry, there are preferably applied to the three primary inputs 108x, 108y and 108z PWM signals of the same amplitude or strength, but which are displaced in the described manner in their phase position through 120°. In accordance with the above formula, these signals are now divided into three and added in the multiphase transformer 100a.

By way of example, the following applies to the calculation of the applied voltages for the multiphase transformer 100a:

$$U\_A = \tfrac{1}{3}U1A + \tfrac{1}{3}U2A + \tfrac{1}{3}U3A.$$

At the individual transformers 102x, 102y and 102z the following relationships apply to the voltages applied:

$$U1A + UxA - UyA = U\_A \quad (1)$$

$$U2A + UyA - UzA = U\_A \quad (2)$$

$$U3A + UzA - UxA = U\_A. \quad (3)$$

Here UxA is the voltage at the primary coil 104x and at the secondary coil 106x, UyA the voltage at the primary coil 104y and at the secondary coil 106y, and UzA the voltage at the primary coil 104z and at the secondary coil 106z. Addition of equations (1) and (3) results in:

$$U1A + U3A + UzA - UyA = 2U\_A,$$

simple rewriting of which results in:

$$UyA - UzA = U1A + U3A - 2U\_A.$$

When inserted in equation (2), this results in:

$$U2A + U1A + U3A - 2U\_A = U\_A,$$

from which follows:

$$U1A + U2A + U3A = 3U\_A.$$

If U1A=1 and U2A=U3A=0, then:

$U\_A = \tfrac{1}{3}$ applies. When inserted in equations (1), (2) and (3), this results in:

$$\tfrac{2}{3} + UxA - UyA = 0 \quad (1)$$

$$UyA - UzA = \tfrac{1}{3} \quad (2)$$

$$UzA - UxA = \tfrac{1}{3}. \quad (3)$$

The voltage relationships of the voltages applied to the single transformers 102x, 102y and 102z are shown, by way of example, for three different pulse widths in FIG. 4, more specifically, in the form of the input voltages U1A, U2A and U3A, applied to the primary inputs, in general, the subphase winding voltages $U_{MW\_1\_1}, \ldots, U_{MW\_1\_N}; \ldots; U_{MW\_M\_1}, \ldots, U_{MW\_M\_N}$ and the output voltage U_A formed by superimposition.

The voltage jump U_A at the motor winding 72a is only one third of the supply voltage $U_S$, but at the threefold frequency $f = 3*f_{PWM}$. This corresponds to a period length $T = \tfrac{1}{3} t_x$, tx being the period length of the PWM signal with the clock frequency $f_{PWM}$ and being calculated at $t_x = 1/f_{PWM}$. The three multiphase transmission devices 98a, 98b and 98c are controlled in a corresponding manner for each motor winding 72a, 72b and 72c, also referred to as motor line.

Figure 5:
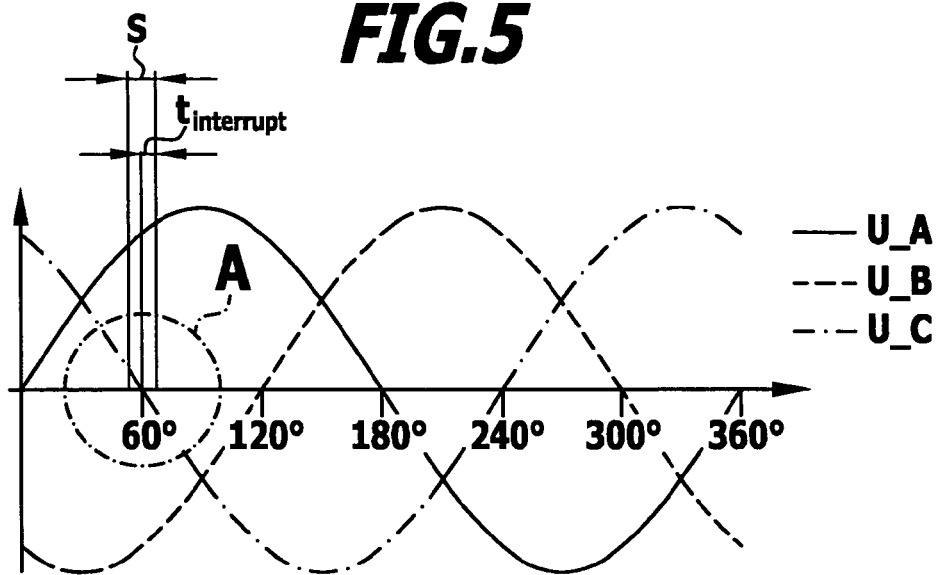
FIG. 5 is a representation of ideal sinusoidal voltage or current supply curves of the motor windings.

To generate a sinusoidal curve of the motor voltages U_A, U_B and U_C, as shown in FIG. 5, the pulse width of the corresponding PWM signals is correspondingly altered, i.e., correspondingly modulated. By controlling the PWM, for example, at 100 kHz, an envelope, namely the desired sinusoidal current supply curve, is generated for controlling the motor 68. Here a frequency of 1 kHz of the sinusoidal signal generated overall by superimposition corresponds to 60,000 revolutions per minute of the motor 68.

The control device 82 therefore forms a current supply device 124, with which each of the M motor windings can be supplied with current sinusoidally or substantially sinusoidally, as shown in FIG. 5.

For optimum supplying of the motor 68 with current it is expedient for a rotor position of the rotor relative to the motor windings 72a, 72b and 72c to be known. The control device 82 therefore comprises a rotor position determining device 126 for determining a rotor position of the electric motor 68 for controlling the M motor windings.

The rotor position determining device 126 comprises a current supply interruption device 128, which interacts with the current supply device 124. In order to determine a position of the rotor of the electric motor 68, at least one of the M motor windings can therefore be cut off for a time interval $t_{interrupt}$ from a power supply of the control device 82. With the rotor position determining device 126, the counter-electromotive motor force (CEMF), i.e., the voltage induced in the currentless motor winding, is measurable during the time interval $t_{interrupt}$, and with a calculating unit 130 included in the rotor position determining device 126, an actual position of the rotor can be calculated in a conventional manner from the measured counter-electromotive force. In particular, with the current supply interruption device 128 the current supply to all motor windings can be simultaneously interrupted for the time interval $t_{interrupt}$ by separating the motor 68 from the power supply. The time interval $t_{interrupt}$ can preferably be prescribed constant or in dependence upon a rotational speed of the motor 68. The current supply interruption device 128 is so constructed that after measurement of the counter-electromotive force all motor lines or motor windings 72a, 72b and 72c that are currentless for this purpose are electrically conductively connected again to the power supply.

In order to obtain as small voltage jumps as possible when the current supply to the motor windings is interrupted, the rotor position determining device 126 is so constructed that the counter-electromotive force is only measurable when the respective motor current I_A, I_B or I_C or the motor voltage U_A, U_B or U_C of one of the M motor windings has dropped to zero. Here the time interval $t_{interrupt}$ is preferably prescribed by $t_{interrupt} = 2\Delta t$, and the measurement of the counter-electromotive force is carried out at one of the M motor windings in the time interval $t_{interrupt}$ such that at the point in time $t_M$ in the case of a continuous supply of current the motor voltage applied to the motor winding would be zero.

Figure 5A:
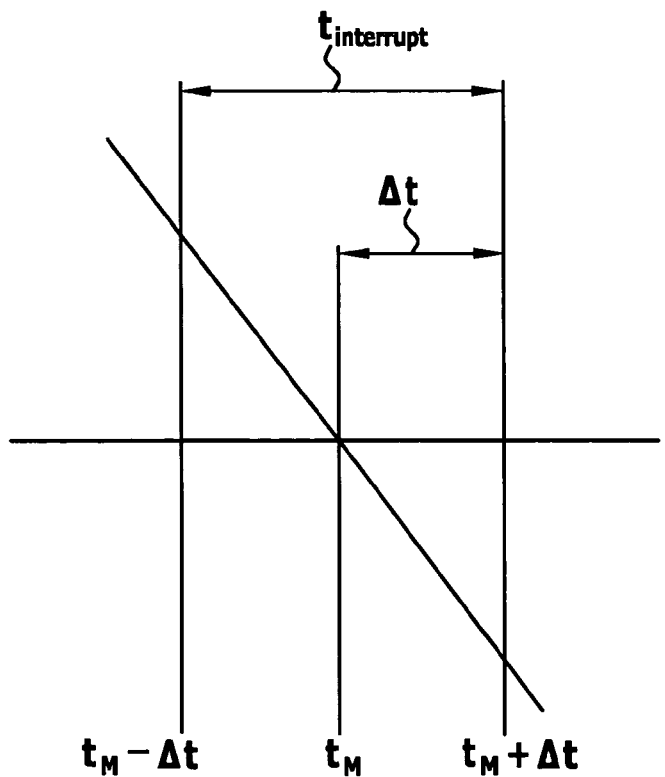
FIG. 5a is an enlarged view of area A in FIG. 5.

The switching-off of the winding voltage at a motor winding is shown, by way of example, in FIG. 5A, in which the voltage drops to zero at the point in time $t_M - \Delta t$ and is only switched on again at the point in time $t_M + \Delta t$. In this way, the current supply, in particular, of the final stage circuits 92a, 92b and 92c can be interrupted at the zero crossing of the generated sinusoidal signal, and via corresponding measuring branches, not shown, of the rotor position determining device 126, which are connected to the motor windings, the measured counter-electromotive force can be evaluated and further processed for controlling purposes, in particular, in cooperation with the controller 84 and the digital signal processor 66.

Figure 7:
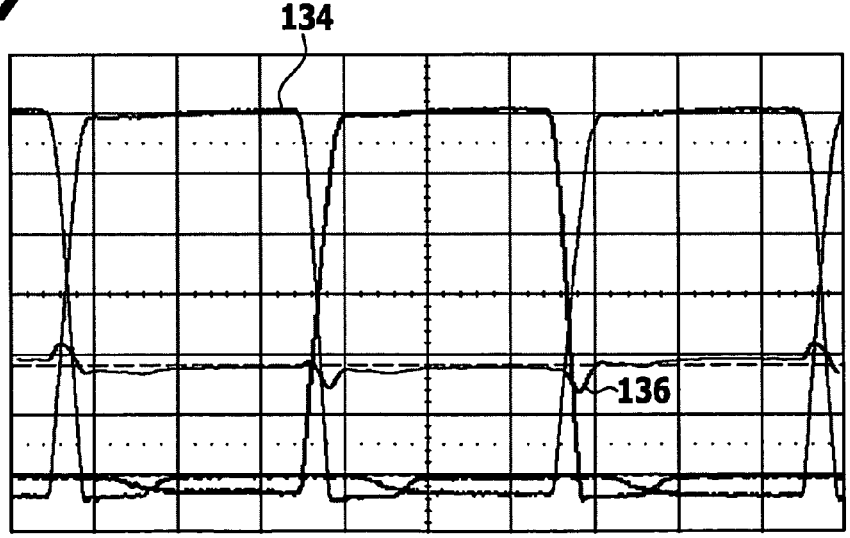
FIG. 7 is a representation, by way of example, of a voltage ripple at a motor winding together with the motor current.
Figure 8:
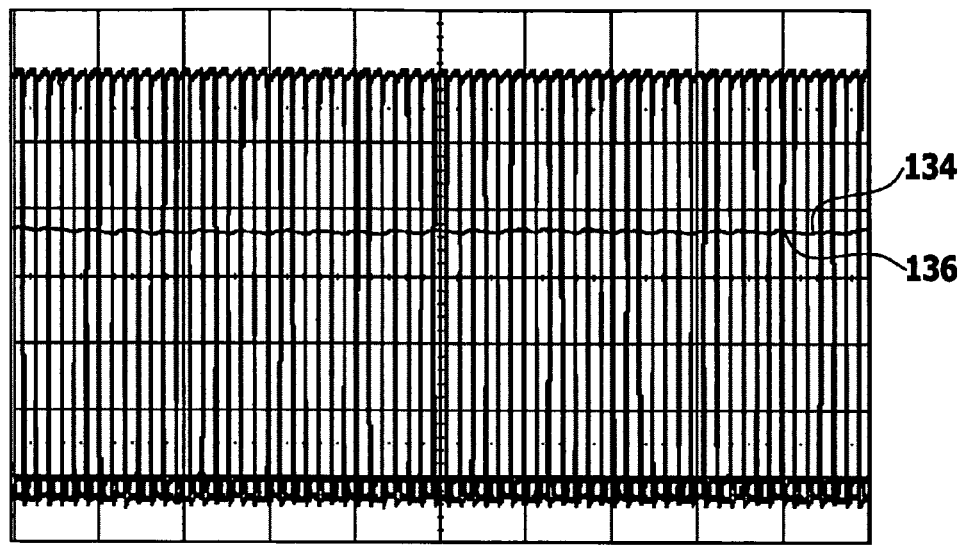
FIG. 8 is a representation, by way of example, of current fluctuations in a motor current of 0.37 amperes in a motor winding.
Figure 9:
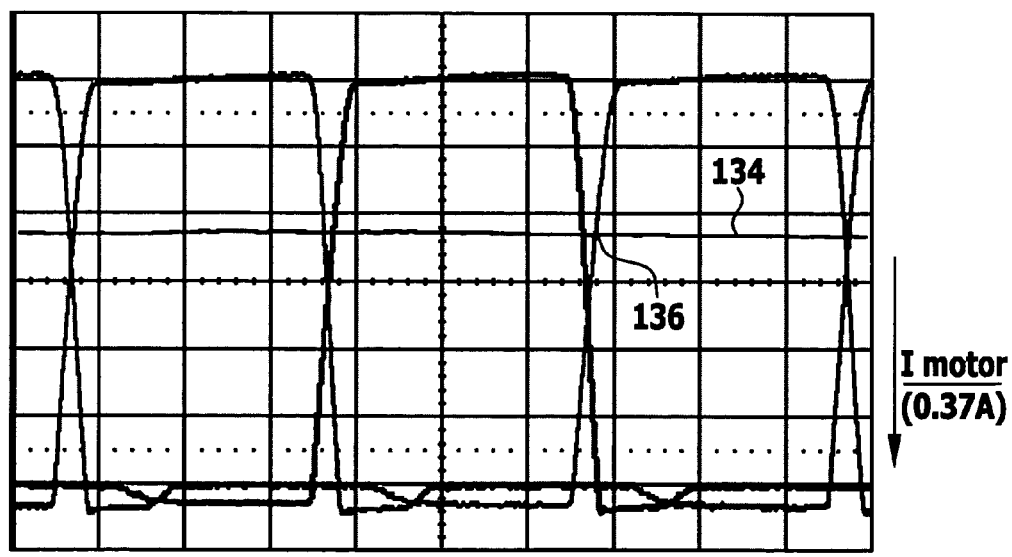
FIG. 9 is a representation, by way of example, of the current ripple as in FIG. 8 with a time resolution increased by a factor of 20.
Figure 10:
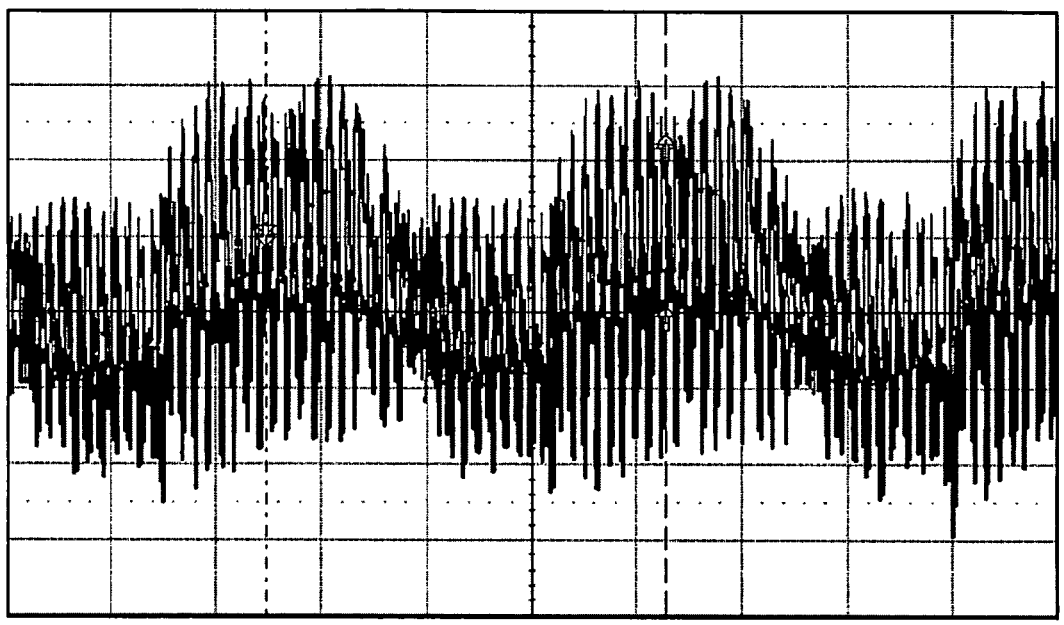
FIG. 10 is a representation, by way of example, of a voltage curve at a motor winding of a drive unit.

There are shown, by way of example, in FIGS. 7 to 9 voltage ripples of the winding voltages U_A (FIG. 7) applied to the motor winding 72a, and the motor current I_A at 0.37 A in the motor winding 72a of the motor 68, which motor current is designated by 134. The current ripple 136 is easy to recognize in FIG. 7. The approximately sinusoidal voltage curve at the motor winding 72a of the motor 68 is shown, by way of example, in FIG. 10. In spite of a prescribed fixed clock frequency $f_{PWM}$ of, for example, 100 kHz, a modulation of the PWM signal, which is higher by the factor N, in the described example with N=3, i.e., 300 kHz, can be effectively realized by the described multiphase PWM. To generate and calculate the individual signals, only processors which can process the PWM clock frequency $f_{PWM}$=100 kHz are, however, required. Electric losses in the electric motor 68 which are proportional to the square of the flowing current I multiplied by the respective resistance R of the motor winding, i.e., $I^2 \cdot R$, can be reduced by the factor $1/N^2$, i.e., by ⅑ in the present example, by the virtual forming of the $N^{th}$-multiple of the signal frequency.

What is claimed is:

1. Surgical motor control device for controlling a surgical drive unit comprising a sensorless electric motor with M motor windings ($R_{MW\_1}, \ldots, R_{MW\_M}$), the motor control device being configured to perform a method for controlling the drive unit, and the motor control device being configured to control the drive unit using a multiphase PWM method, the motor control device comprising:
   a signal generating device with which a PWM signal ($S_{PWM\_1}, \ldots, S_{PWM\_M}$) is generatable for each of the M motor windings ($R_{MW\_1}, \ldots, R_{MW\_M}$), and with which each of the M PWM signals ($S_{PWM\_1}, \ldots, S_{PWM\_M}$) is divisible into N subphase signals ($S_{PWM\_1\_1}, \ldots, S_{PWM\_1\_N}; \ldots; S_{PWM\_M\_1}, \ldots, S_{PWM\_M\_N}$) which are displaced in their phase position relative to one another through 360°/N in each case; and
   a multiphase transformer, with which the N subphase signals ($S_{PWM\_1\_1}, \ldots, S_{PWM\_1\_N}; \ldots; S_{PWM\_M\_1}, \ldots, S_{PWM\_M\_N}$) associated with a respective one of the M motor windings ($R_{MW\_1}, \ldots, R_{MW\_M}$) are convertible into N subphase winding voltages ($U_{MW\_1\_1}, \ldots, U_{MW\_1\_N}; \ldots; U_{MW\_M\_1}, \ldots, U_{MW\_M\_N}$) which are displaced in their phase position relative to one another through 360°/N in each case, with which in order to generate a current flow ($I_{MW\_1}, \ldots, I_{MW\_M}$) through each of the M motor windings ($R_{MW\_1}, \ldots, R_{MW\_M}$) a respective winding voltage ($U_{MW\_1}, \ldots, U_{MW\_M}$) is applied to each of the M motor windings ($R_{MW\_1}, \ldots, R_{MW\_M}$), and with which the N subphase winding voltages ($U_{MW\_1\_1}, \ldots, U_{MW\_1\_N}; \ldots; U_{MW\_M\_N}$) associated with a respective one of the M motor windings are separately superimposed for each of the M motor windings ($R_{MW\_1}, \ldots, R_{MW\_M}$), for formation of the respective winding voltage ($U_{MW\_1}, \ldots, U_{MW\_M}$) that is directly applied to the respective motor winding ($R_{MW\_1}, \ldots, R_{MW\_M}$), in order to generate the winding current ($I_{MW\_1}, \ldots, I_{MW\_M}$); wherein a power loss at each motor winding, caused by current ripple, is reduced by a factor of $1/N^2$.

2. Surgical motor control device in accordance with claim 1, wherein the multiphase transformer is so configured that the N subphase winding voltages ($U_{MW\_1\_1}, \ldots, U_{MW\_1\_N}; \ldots; U_{MW\_M\_1}, \ldots, U_{MW\_M\_N}$) associated with a respective one of the M motor windings ($R_{MW\_1}, \ldots, R_{MW\_M}$) are superimposable in a such a way for formation of the respective winding voltage ($U_{MW\_1}, \ldots, U_{MW\_M}$) that a signal amplitude of the winding voltage ($U_{MW\_1}, \ldots, U_{MW\_M}$) is 1/N of a signal amplitude of the respective N subphase winding voltages ($U_{MW\_1\_1}, \ldots, U_{MW\_1\_N}; \ldots; U_{MW\_M\_1}, \ldots, U_{MW\_M\_N}$).

3. Surgical motor control device in accordance with claim 2, comprising M multiphase transmission devices for superimposing the total of M*N subphase winding voltages ($U_{MW\_1\_1}, \ldots, U_{MW\_1\_N}; \ldots; U_{MW\_M\_1}, \ldots, U_{MW\_M\_N}$) for formation of the winding voltages ($U_{MW\_1}, \ldots, U_{MW\_M}$).

4. Surgical motor control device in accordance with claim 3, wherein each of the M multiphase transmission devices comprises N single phase transmission devices.

5. Surgical motor control device in accordance with claim 4, wherein each single phase transmission device is in the form of a single transformer and wherein each of the N single transformers of one of the M multiphase transmission devices comprises a primary coil with a primary input and a primary output and a secondary coil inductively coupled to the primary coil with a secondary input and a secondary output.

6. Surgical motor control device in accordance with claim 1, comprising a clock generator device for prescribing a PWM clock frequency $f_{PWM}$ for performing the PWM method.

7. Surgical motor control device in accordance with claim 6, wherein the signal generating device interacts in such a way with the clock generator device that the N subphase signals ($S_{PWM\_1\_1}, \ldots, S_{PWM\_1\_N}; \ldots; S_{PWM\_M\_1}, \ldots, S_{PWM\_M\_N}$) are generatable with the PWM clock frequency $f_{PWM}$.

8. Surgical motor control device in accordance with claim 1, comprising a rotor position determining device for determining a rotor position of the electric motor in order to control a supplying of current to the M motor windings ($R_{MW\_1}, \ldots, R_{MW\_M}$).

9. Surgical motor control device in accordance with claim 8, wherein:
   the rotor position determining device comprises a current supply interruption device with which at least one of the M motor windings ($R_{MW\_1}, \ldots, R_{MW\_M}$) is separable from a power supply of the drive unit for a time interval $t_{interrupt}$ in order to determine the position of the rotor of the electric motor,
   a counter-electromotive force in at least one of the M motor windings ($R_{MW\_1}, \ldots, R_{MW\_M}$) is measurable with the rotor position determining device during the time interval $t_{interrupt}$,
   the rotor position determining device comprises a calculating unit for calculating an actual position of the rotor from the measured counter-electromotive force, and
   the current supply interruption device is so configured that after measurement of the counter-electromotive force all M motor windings ($R_{MW\_1}, \ldots, R_{MW\_M}$) are electrically conductively connectable again to the power supply of the drive unit.

10. Surgical motor control device in accordance with claim 8, wherein:
   the rotor position determining device comprises a current supply interruption device with which at least one of the M motor windings ($R_{MW\_1}, \ldots, R_{MW\_M}$) is separable from a power supply of the drive unit for a time interval $t_{interrupt}$ in order to determine the position of the rotor of the electric motor,
   a counter-electromotive force in at least one of the M motor windings ($R_{MW\_1}, \ldots, R_{MW\_M}$) is measurable with the rotor position determining device during the time interval $t_{interrupt}$, and wherein
   the rotor position determining device comprises a calculating unit for calculating an actual position of the rotor from the measured counter-electromotive force, and
   the rotor position determining device is so configured that the counter-electromotive force is only measurable when the motor current ($I_{MW\_1}, \ldots, I_{MW\_M}$) of at least one of the M motor windings ($R_{MW\_1}, \ldots, R_{MW\_M}$) has dropped to zero.

11. Surgical motor control device in accordance with claim 8, wherein:
   the rotor position determining device comprises a current supply interruption device with which at least one of the M motor windings ($R_{MW\_1}, \ldots, R_{MW\_M}$) is separable from a power supply of the drive unit for a time interval $t_{interrupt}$ in order to determine the position of the rotor of the electric motor, a counter-electromotive force in at least one of the M motor windings ($R_{MW\_1}, \ldots, R_{MW\_M}$) is measurable with the rotor position determining device during the time interval $t_{interrupt}$, and wherein the rotor position determining device comprises a calculating unit for calculating an actual position of the rotor from the measured counter-electromotive force, and the rotor position determining device is so configured that the measurement of the counter-electromotive force at one of the M motor windings ($R_{MW\_1}, \ldots, R_{MW\_M}$) is performable in a time interval $t_M \pm \Delta t$, the motor voltage ($U_{MW\_1}, \ldots, U_{MW\_M}$) applied to the motor winding ($R_{MW\_1}, \ldots, R_{MW\_M}$) being zero at the point in time $t_M$.

12. Method for controlling a surgical drive unit with a sensorless electric motor comprising a rotor and M motor windings, the method being a multiphase PWM method and comprising:

generating a PWM signal ($S_{PWM\_1}, \ldots, S_{PWM\_M}$) for each of the M motor windings, dividing each of the M PWM signals ($S_{PWM\_1}; \ldots; S_{PWM\_M}$) into N subphase signals ($S_{PWM\_1\_1}, \ldots, S_{PWM\_1\_N}; \ldots; S_{PWM\_M\_1}, \ldots, S_{PWM\_M\_N}$) which are displaced in their phase position relative to one another through 360°/N in each case, converting, at a multiphase transformer, the N subphase signals ($S_{PWM\_1\_1}, \ldots, S_{PWM\_1\_N}; \ldots; S_{PWM\_M\_1}, \ldots, S_{PWM\_M\_N}$) associated with a respective one of the M motor windings into N subphase winding voltages ($U_{MW\_1\_1}, \ldots, U_{MW\_1\_N}; \ldots; U_{MW\_M\_1}, \ldots, U_{MW\_M\_N}$) which are displaced in their phase position relative to one another through 360°/N in each case, wherein:

in order to generate a current flow ($I_{MW\_1}, \ldots, I_{MW\_M}$) through each of the M motor windings ($R_{MW\_1}, \ldots, R_{MW\_M}$) a respective winding voltage ($U_{MW\_1}, \ldots, U_{MW\_M}$) is applied to each of the M motor windings ($R_{MW\_1}, \ldots, R_{MW\_M}$), and the N subphase winding voltages ($U_{MW\_1\_1}, \ldots, U_{MW\_1\_N}; \ldots; U_{MW\_M\_1}, \ldots, U_{MW\_M\_N}$) associated with a respective one of the M motor windings are separately superimposed, for each of the M motor windings ($R_{MW\_1}, \ldots, R_{MW\_M}$), for formation of the respective winding voltage ($U_{MW\_1}, \ldots, U_{MW\_M}$) that is applied to the respective motor winding ($R_{MW\_1}, \ldots, R_{MW\_M}$), in order to generate the winding current ($I_{MW\_1}, \ldots, I_{MW\_M}$), and a power loss at each motor winding, caused by current ripple, is reduced by a factor of $1/N^2$.

13. Method in accordance with claim 12, wherein each of the M motor windings is sinusoidally or approximately sinusoidally supplied with current using the multiphase PWM method.

14. Method in accordance with claim 12, wherein the N subphase winding voltages ($U_{MW\_1\_1}, \ldots, U_{MW\_1\_N}; \ldots; U_{MW\_M\_1}, \ldots, I_{MW\_M\_N}$) associated with a respective one of the M motor windings are superimposed in a such a way for formation of the respective winding voltage ($U_{MW\_1}, \ldots, U_{MW\_M}$) that a signal amplitude of the winding voltage ($U_{MW\_1}, \ldots, U_{MW\_M}$) is 1/N of a signal amplitude of the respective N subphase winding voltages ($U_{MW\_1\_1}, \ldots, U_{MW\_1\_N}; \ldots; U_{MW\_M\_1}, \ldots, U_{MW\_M\_N}$).

15. Method in accordance with claim 12, wherein the total of M*N subphase winding voltages ($U_{MW\_1\_1}, \ldots, U_{MW\_1\_N}; \ldots; U_{MW\_M\_1}, \ldots, U_{MW\_M\_N}$) are superimposed by means of M multiphase transmission devices for formation of the winding voltages ($U_{MW\_1}, \ldots, U_{MW\_M}$).

16. Method in accordance with claim 12, wherein a rotor position of the electric motor is determined in order to control a supplying of current to the M motor windings.

17. Method in accordance with claim 16, wherein:

in order to determine the position of the rotor of the electric motor, at least one of the M motor windings is separated from a power supply of the drive unit for a time interval $t_{interrupt}$, a counter-electromotive force in at least one of the M motor windings is measured during the time interval $t_{interrupt}$, and an actual position of the rotor is calculated from the measured counter-electromotive force.

18. Method in accordance with claim 17, wherein the measurement of the counter-electromotive force at one of the M motor windings ($R_{MW\_1}, \ldots, R_{MW\_M}$) is performed in a time interval $t_M \pm \Delta t$, the point in time $t_M$ being so selected that the motor voltage ($U_{MW\_1}, \ldots, U_{MW\_M}$) applied to the motor winding ($R_{MW\_1}, \ldots, R_{MW\_M}$) at the point in time $t_M$ is zero.

19. Surgical drive system comprising at least one control device and at least one surgical drive unit connectable to and controllable by the control device and/or at least one surgical instrument comprising a surgical drive unit, the at least one drive unit comprising a sensorless electric motor with a rotor and M motor windings, the control device being configured to control the drive unit using a method for controlling the drive unit, the method for controlling being a multiphase PWM method, the control device being in the form of a motor control device and comprising:

a signal generating device with which a PWM signal is generatable for each of the M motor windings, and with which each of the M PWM signals is divisible into N subphase signals which are displaced in their phase position relative to one another through 360°/N in each case, and a multiphase transformer, with which the N subphase signals associated with a respective one of the M motor windings are convertible into N subphase winding voltages which are displaced in their phase position relative to one another through 360°/N in each case, with which in order to generate a current flow through each of the M motor windings a respective winding voltage is applied to each of the M motor windings, and with which the N subphase winding voltages associated with a respective one of the M motor windings are separately superimposed for each of the M motor windings, for formation of the respective winding voltage that is directly applied to the respective motor winding, in order to generate the winding current; wherein a power loss at each motor winding, caused by current ripple, is reduced by a factor of $1/N^2$.

* * * * *

UNITED STATES PATENT AND TRADEMARK OFFICE
CERTIFICATE OF CORRECTION

PATENT NO. : 8,493,009 B2
APPLICATION NO. : 12/798449
DATED : July 23, 2013
INVENTOR(S) : Hafner et al.

Page 1 of 1

It is certified that error appears in the above-identified patent and that said Letters Patent is hereby corrected as shown below:

In the Claims:

Claim 1, Column 17, lines 21-22: "each of the M PWM signals ($S_{PMW\_1}$, ..., $S_{PMW\_M}$) is divisible into N subphase signals ($S_{PWM\_1}$, ...,", should read -- each of the M PWM signals ($S_{PWM\_1}$, ..., $S_{PWM\_M}$) is divisible into N subphase signals ($S_{PWM\_1\_1}$, ..., --

Claim 1, Column 17, line 39: "ages ($U_{MW\_1\_1}$, ..., $U_{MW\_1\_N}$; ...; $U_{MW\_M\_N}$) asso-" should read -- ages ($U_{MW\_1\_1}$, ..., $U_{MW\_1\_N}$; ...; $U_{MW\_M\_1}$, ..., $U_{MW\_M\_N}$) asso- --

Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,493,009 B2  
APPLICATION NO. : 12/798449  
DATED : July 23, 2013  
INVENTOR(S) : Hafner et al.

It is certified that error appears in the above-identified patent and that said Letters Patent is hereby corrected as shown below:

In the Claims:

Claim 1, Column 17, lines 21-22: "each of the M PWM signals ($S_{PMW\_1}$, ..., $S_{PWM\_M}$) is divisible into N subphase signals ($S_{PWM\_1}$, ...," should read -- each of the M PWM signals ($S_{PWM\_1}$, ..., $S_{PWM\_M}$) is divisible into N subphase signals ($S_{PWM\_1\_1}$, ..., --

Claim 1, Column 17, line 39: "ages ($U_{MW\_1\_1}$, ..., $U_{MW\_1\_N}$; ...; $U_{MW\_M\_N}$) asso-" should read -- ages ($U_{MW\_1\_1}$, ..., $U_{MW\_1\_N}$; ...; $U_{MW\_M\_1}$, ..., $U_{MW\_M\_N}$) asso- --

This certificate supersedes the Certificate of Correction issued November 26, 2013.

Signed and Sealed this  
Eleventh Day of February, 2014

Michelle K. Lee  
*Deputy Director of the United States Patent and Trademark Office*